(12) United States Patent
Cabantchik et al.

(10) Patent No.: US 9,291,619 B2
(45) Date of Patent: Mar. 22, 2016

(54) METHOD FOR DETECTING NON-TRANSFERRIN BOUND IRON

(71) Applicants:Ioav Zvi Cabantchik, Har Adar (IL); William Breuer, Zur Hadassa (IL)

(72) Inventors: Ioav Zvi Cabantchik, Har Adar (IL); William Breuer, Zur Hadassa (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 647 days.

(21) Appl. No.: 13/644,565

(22) Filed: Oct. 4, 2012

(65) Prior Publication Data

US 2013/0203800 A1 Aug. 8, 2013

Related U.S. Application Data

(60) Provisional application No. 61/542,882, filed on Oct. 4, 2011.

(51) Int. Cl.
*G01N 33/53* (2006.01)
*G01N 33/84* (2006.01)
*G01N 33/00* (2006.01)

(52) U.S. Cl.
CPC ............ *G01N 33/5308* (2013.01); *G01N 33/84* (2013.01); *G01N 2800/50* (2013.01); *G01N 2800/52* (2013.01)

(58) Field of Classification Search
CPC .......... G01N 33/5308; G01N 2800/52; G01N 2800/50; G01N 33/84
USPC ..................................... 514/292; 436/74, 501
See application file for complete search history.

(56) References Cited

U.S. PATENT DOCUMENTS

2003/0104491 A1* 6/2003 Cabantchik et al. ........... 435/7.7
2006/0105394 A1* 5/2006 Pomara .......................... 435/7.1

FOREIGN PATENT DOCUMENTS

WO WO 2004/040252 5/2004

OTHER PUBLICATIONS

Gosriwatana et al. "Quantification of Non-Transferrin-Bound Iron in the Presence of Unsaturated Transferrin", Analytical Biochemistry, 273: 212-220, 1999.
Kolb et al. "Non-Transferrin Bound Iron Measurement Is Influenced by Chelator Concentration", Analytical Biochemistry, 385: 13-19, 2009.
Breuer et al. "Non-Transferrin Bound Iron in Thalassemia: Differential Detection of Redox Active Forms in Children and Older Patients", American Journal of Hematology, 87: 55-61, 2012.

\* cited by examiner

*Primary Examiner* — Rebecca M Fritchman

(57) ABSTRACT

A method of quantifying non-transferrin bound iron (NTBI) in a biological fluid is provided, the method comprising:
(a) contacting a sample of the biological fluid with a reducing agent to obtain redox-active iron;
(b) contacting the sample of the biological fluid with a nitrilotriacetate (NTA) at a concentration of 0.4-2 mM to mobilize non-transferrin bound iron including redox inactive and the redox active iron in the sample;
(c) contacting the sample of the biological fluid of step (b) with an indicator including an iron binding moiety and fluorophore; and
(d) detecting and quantifying a fluorescent signal of the fluorophore thereby quantifying the NTBI in the biological sample.

28 Claims, 7 Drawing Sheets

METHOD FOR DETECTING NON-TRANSFERRIN BOUND IRON

RELATED APPLICATION

This application claims the benefit of priority under 35 USC §119(e) of U.S. Provisional Patent Application No. 61/542,882 filed Oct. 4, 2011, the contents of which are incorporated herein by reference in their entirety.

FIELD AND BACKGROUND OF THE INVENTION

The present invention, in some embodiments thereof, relates to a method for detecting non-transferrin bound iron.

The association between iron overload diseases and the occurrence of iron forms in plasma that are not associated with transferrin (Tf) bound iron (TBI) is a well-documented phenomenon [1,2]. These forms, referred collectively as non-TBI or NTBI, appear in plasma when Tf binding capacity for iron is exceeded due to massive iron overload, such as occurs in thalassemia major [3] and other congenital anemias [4], which require repeated blood transfusions, or bone marrow failure where iron utilization is inefficient [5]. NTBI may also occur in primary iron overload such as thalassemia intermedia or hemochromatosis even in the setting of <100% Tf saturation [6,7,8], due apparently to formation of insoluble polynuclear ferrihydrate species [9] and complexes with modified albumin [10] that are inaccessible to Tf.

The initial study of NTBI in the serum of thalassemia patients [11] and others that followed [reviewed in 12] led to the recognition that NTBI may be an important indicator of systemic iron overload and source of tissue iron accumulation. However, studies have highlighted difficulties in analyzing NTBI in a complex medium, which necessitated usage of chelating or mobilizing agents to solubilize it and facilitate its separation from TBI by ultrafiltration, prior to chemical detection. NTBI appears in iron overloaded plasma in multiple forms, some easily filterable via size exclusion leaving others protein bound, some complexed to small organic ligands which, in turn, might be free or adsorbed to proteins [9,10]. Moreover, the composition of NTBI might vary with the degree and source of iron overload, treatment of the patient with chelator or phlebotomy and the sample storage conditions which, ideally, should preserve both the TBI and the NTBI components. Due to the chemical complexity and potential clinical importance of NTBI, a number of alternative methods have been developed for its detection [12,13] with the objective of obtaining a better measure of the total content of NTBI in a patient sample. In general these methods have relied on the principle of using a powerful chelator or high concentrations of mobilizing agents (with or without a filtration step), in order to maximize NTBI's accessibility to the various iron-detecting reagents [11,14-16].

The present inventors have previously developed an assay for quantifying the overtly labile forms of NTBI in plasma or serum, namely endogenous forms that are both redox-active, exchangeable and chelatable, which they defined as labile plasma iron or LPI [8,17]. The chemical properties of LPI in native plasma were assumed to be pathophysiologically relevant as a source of tissue iron overload because 1. ligand exchangeability is a precondition for metal transfer across membranes via transporters/channels and 2. LPI can serve as direct chelator target [1]. The advantage of the LPI assays is their performance on native plasma or serum, which essentially avoids potential complications associated with the use of high concentrations of iron-mobilizing agents or filtration steps by other NTBI assays [14,15]. The disadvantage of using just native plasma relates to variable plasma components (e.g. citrate, uric acid and albumin) that have the potential to dampen LPI measurements.

OTHER RELATED BACKGROUND ART

Kolb et al. 2009 Analytical Biochemistry 385:13-19;
Gosriwatana 1999 Analytical Biochemistry 273:212-220.

SUMMARY OF THE INVENTION

According to an aspect of some embodiments of the present invention there is provided a method of quantifying non-transferrin bound iron (NTBI) in a biological fluid, the method comprising:

(a) contacting a sample of the biological fluid with a reducing agent to obtain redox-active iron;

(b) contacting the sample of the biological fluid with a nitrilotriacetate (NTA) at a concentration of 0.4-2 mM to mobilize non-transferrin bound iron including redox inactive and the redox active iron in the sample;

(c) contacting the sample of the biological fluid of step (b) with an indicator including an iron binding moiety and fluorophore; and (d) detecting and quantifying a fluorescent signal of the fluorophore thereby quantifying the NTBI in the biological sample.

According to an aspect of some embodiments of the present invention there is provided a method of treating a subject having a disorder associated with abnormal levels of free iron in a biological fluid, the method comprising:

(i) quantifying free iron levels (NTBI) in a biological fluid of the subject according to the method described herein; and (ii) treating the subject with a chelation therapy.

According to some embodiments of the invention, (i) is effected prior to (ii).

According to some embodiments of the invention, (i) is effected following (ii).

According to some embodiments of the invention, (i) is effected prior to (ii) and following (ii).

According to some embodiments of the invention, the concentration of the NTA is 0.5-1 mM.

According to some embodiments of the invention, the iron binding moiety comprises an iron binding protein selected from the group consisting of, lactoferrin, transferrin, ferritin, Ferric uptake repressor (FUR) protein, calcineurin, acid phosphatase and ferredoxin.

According to some embodiments of the invention, the iron binding moiety comprises an iron chelator selected from the group consisting of desferrioxamine, Deferasirox, FBS0701, phenanthroline, ethylene diamine tetra-acetic acid (EDTA), diethylene triamine-pentaacetic acid (DTPA) and N,N'-bis [2-hydroxybenzoyl]ethylene diamine-N,N'-diacetic acid (HBED).

According to some embodiments of the invention, the indicator comprises a chimeric protein.

According to some embodiments of the invention, the biological fluid is a serum or a plasma.

According to some embodiments of the invention, the biological fluid is selected from the group consisting of as blood, serum, plasma, lymph, bile fluid, urine, saliva, sputum, synovial fluid, semen, tears, cerebrospinal fluid, bronchioalveolar large fluid, ascites fluid and pus.

According to some embodiments of the invention, the biological fluid is of a subject having thalassemia.

According to some embodiments of the invention, the biological fluid is of a subject having a medical condition selected from the group consisting of hemolytic diseases hemoglobinopathies, thalassemia, thalassemia major, anemia, sickle cell anemia, aplastic anemia, megaloblastic anemia, myelodysplasia, diseases which require repeated transfusions, diseases which require dialysis, hereditary hemachromatosis, cancer, heart diseases, Megaloblastic Dysplasia Syndrome (MDS), iron poisoning and rheumatoid arthritis and diabetes.

According to some embodiments of the invention, the signal generating moiety comprises a fluorophore selected from the group consisting of Fluorescein, Rhodamine, nitrobenzfurazan, fluorogenic β-galactosidase, a green fluorescent protein and coumarin.

According to some embodiments of the invention, the method further comprises contacting the sample with an apotransferrin binding metal other than iron prior to step (b).

According to some embodiments of the invention, the apotransferrin binding metal other than iron is cobalt or gallium.

According to some embodiments of the invention, the reducing agent is selected from the group consisting of ascorbic acid, dithionite, dithiothreitol or mercaptoacetic acid.

According to some embodiments of the invention, the indicator is attached to a microparticle.

According to some embodiments of the invention, the detecting is effected by FACS.

According to some embodiments of the invention, the detecting is effected by a fluorescence plate reader.

According to some embodiments of the invention, the biological fluid is of a subject has not been exposed to chelation treatment.

According to some embodiments of the invention, the biological fluid is of a subject exposed to chelation treatment not more than 24 hours prior to quantifying.

According to an aspect of some embodiments of the present invention there is provided a method of quantifying free iron levels in a biological fluid of a subject in need thereof, the method comprising:

(a) analyzing labile plasma iron (LPI) in a first biological sample of the biological fluid of the subject; and (b) analyzing NTBI in a second biological sample of the biological fluid of the subject, thereby quantifying free iron levels in the biological fluid of the subject.

According to an aspect of some embodiments of the present invention there is provided a method of treating a subject having a disorder associated with abnormal levels of free iron in a biological fluid, the method comprising:

(i) quantifying free iron levels (NTBI+LPI) in a biological fluid of the subject according to the method described herein; and (ii) treating the subject with a chelation therapy.

According to some embodiments of the invention, (i)(b) is affected prior to (ii) and (i)(a) is effected following (ii).

According to some embodiments of the invention, (i)(a) is effected concomitantly with (i)(b).

According to some embodiments of the invention, analyzing the NTBI is effected according to the method described herein.

According to some embodiments of the invention, analyzing the LPI is effected by:

(a) contacting the first sample of the biological fluid with a reducing agent to obtain redox active iron;

(c) contacting the sample of the biological fluid of step (b) with an indicator including an iron binding moiety and fluorophore; and (d) detecting and quantifying a fluorescent signal of the fluorophore thereby quantifying the LPI in the biological sample According to an aspect of some embodiments of the present invention there is provided a method of determining a presence, absence or risk of a disorder associated with abnormal levels of free iron in a biological fluid of a subject, the method comprising:

(a) determining levels of the free iron (NTBI and optionally LPI) in the biological fluid of the subject according to any of the methods described herein; and (b) determining in the subject based on the levels a presence, absence or risk of the disorder associated with abnormal free iron levels.

According to an aspect of some embodiments of the present invention there is provided a method of determining subject's compliance to chelation therapy, the method comprising:

(a) retrieving a biological fluid of a subject in need thereof 2-24 hours following alleged administration of the chelation therapy; and (b) quantifying free iron levels in the biological fluid of the subject according to the method described herein, wherein an increase in NTBI level compared to LPI level is indicative of subject's compliance.

According to an aspect of some embodiments of the present invention there is provided a method of determining efficacy of treatment of a disorder associated with abnormal levels of free iron in a biological fluid;

(a) treating a subject in need thereof using a medicament for the disorder associated with abnormal free iron levels; and (b) determining levels of the free iron in a biological fluid or cells of the subject according to any of the methods described herein, wherein a change in the levels following the treating is indicative of treatment efficacy.

According to some embodiments of the invention, the medicament comprises iron chelation therapy, and whereas a reduction in the levels following the therapy is indicative of efficacious treatment.

According to some embodiments of the invention, the disorder associated with abnormal levels of free iron is selected from the group consisting of hemolytic diseases hemoglobinopathies, thalassemia, thalassemia major, anemia, sickle cell anemia, aplastic anemia, megaloblastic anemia, myelodysplasia, diseases which require repeated transfusions, diseases which require dialysis, hereditary hemachromatosis, cancer, heart diseases, Megaloblastic Dysplasia Syndrome (MDS), iron poisoning, end stage kidney disease, cancer, transplantation-associated anemia, rheumatoid arthritis and diabetes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1:
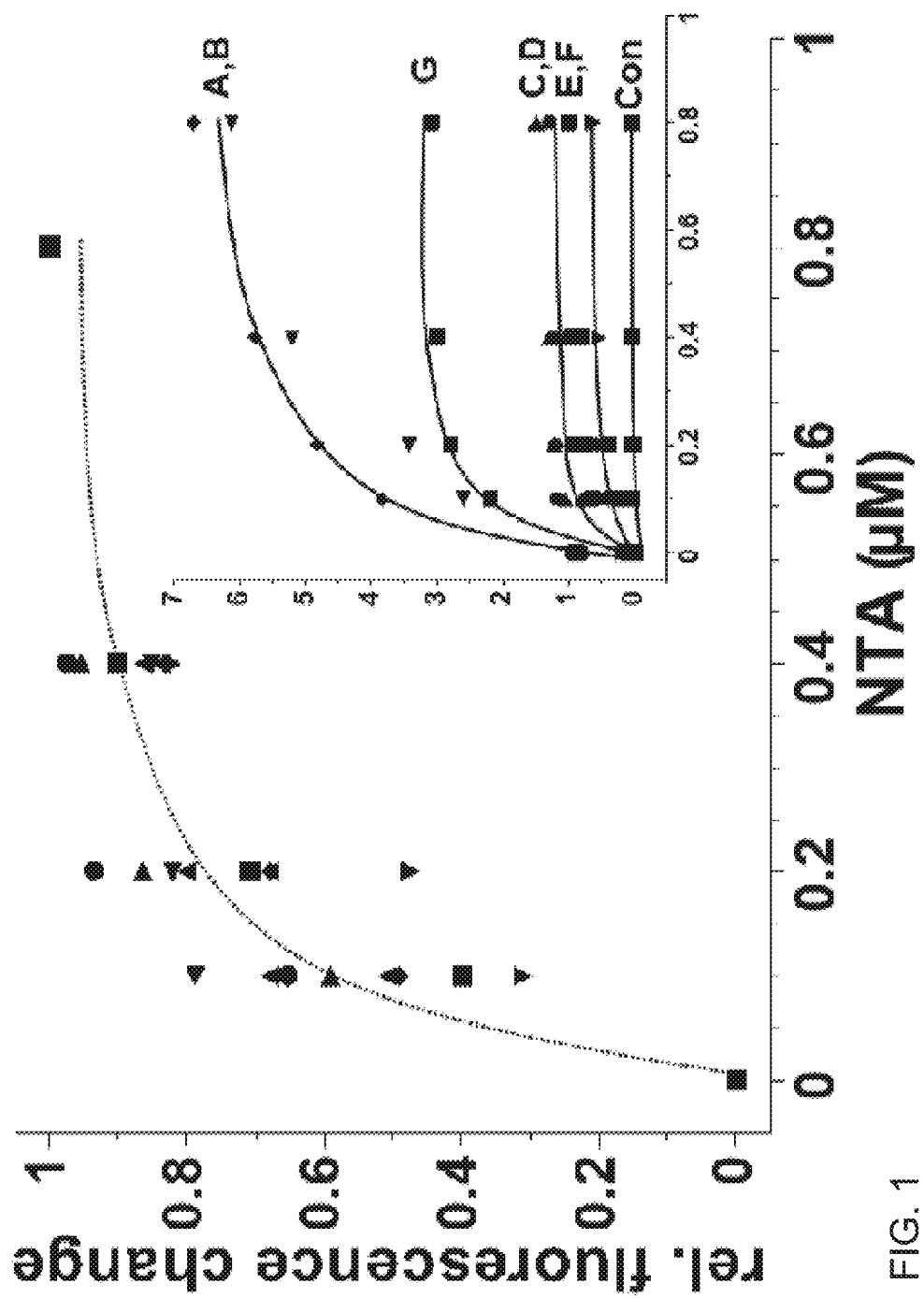
FIG. 1 is a graph showing the effect of NTA on LPI values in thalassemic sera: concentration dependence. Seven sera from thalassemic patients (children from EHG, A-G; each designated by a different symbol) and two healthy controls were assayed for LPI, in the presence of increasing concentrations of NTA in the assay reagents. All LPI values were calculated from the same calibration curve, which was equally applicable for all of the NTA concentrations used. Inset: The fluorescence changes that are chelator sensitive i.e. iron-dependent (given in arbitrary units a.u.) are plotted vs. NTA concentration. The fluorescence changes obtained at different NTA concentrations relative to the changes obtained at 0.8 mM NTA are plotted in the main figure. The hyperbolic non-linear square fit ($r^2$=0.935) yielded a plateau value of 1.12±0.05, a half max concentration of NTA at 0.10 ±0.05 mM.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

DETAILED DESCRIPTION OF THE PREFERRED EMBODIMENTS

The present invention, in some embodiments thereof, relates to a method for detecting non-transferrin bound iron.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The association between iron overload diseases and the occurrence of iron forms in plasma that are not associated with transferrin (TO bound iron (TBI) is a well-documented phenomenon. The measurement of NTBI at its various forms is a clinically acceptable parameter in the diagnosis and treatment of a number of indications associated with free-iron overload.

The present inventors have previously introduced an assay for quantifying the overtly labile forms of NTBI in plasma or serum, namely endogenous forms that are both redox-active, exchangeable and chelatable, defined as labile plasma iron or LPI [8,17]. The chemical properties of LPI in native plasma were assumed to be pathophysiologically relevant as a source of tissue iron overload because, first, ligand exchangeability is a precondition for metal transfer across membranes via transporters/ channels; and second, LPI can serve as direct chelator target [1]. The advantage of the LPI assays is their performance on native plasma or serum, which essentially avoids potential complications associated with the use of high concentrations of iron-mobilizing agents or filtration steps by other NTBI assays [14,15]. The disadvantage of using just native plasma relates to variable plasma components (e.g. citrate, uric acid and albumin) that have the potential to dampen LPI measurements.

While reducing the present invention to practice, the present inventors have shown through laborious experimentation and screening that the effects of those plasma components can be experimentally mitigated in the presence of mild metal mobilizing agents added to the LPI assay reagent.

As shown herein below and in the Examples section which follows, at concentrations <0.5 mM, nitrilotriacetic acid (NTA) overrode the effects of plasma albumin, citrate and uric acid in different patient samples Importantly, mobilization did not cause any detectable release of iron from fully saturated Tf or interfered significantly with neutralization of LPI by clinically used chelators. The observed effect is attributable to mobilization of iron from physiological ligands such as citrate and albumin to nitriloacetate, leading to improved detection of the metal's redox-activity. The term LPI was used to denote the native and endogenously redox-active forms of NTBI; and enhanced LPI (eLPI) was used to denote the forms of NTBI that are detectable in the presence of NTA. eLPI is synonymously referred to as NTBI. As eLPI values correlate reasonably well with deferrioxamine-chelatable iron (DCI) in sera [8], eLPI is effectively a measure of DFO-chelatable NTBI in plasma. The combination of LPI and eLPI measurements in a single assay was particularly useful for identifying patients who show apparently low or borderline LPI levels, in spite of severe iron overload and presence of NTBI in the serum. Comparative analysis of poly-transfused thalassemia major patients aged from 3 to 61 years indicated significant levels of eLPI in all age groups, but a much lower frequency of LPI in children and adolescents-young adults (3-28 yrs) compared to adults (>30 yrs).

Thus, according to an aspect of the invention there is provided a method of quantifying non-transferrin bound iron (NTBI) in a biological fluid, the method comprising:

(a) contacting a sample of the biological fluid with a reducing agent to obtain redox-active iron;

(b) contacting said sample of the biological fluid with a nitrilotriacetate (NTA) at a concentration of 0.4-2 mM to mobilize non-transferrin bound iron including redox inactive and said redox active iron in said sample;

(c) contacting said sample of the biological fluid of step (b) with an indicator including an iron binding moiety and fluorophore; and (d) detecting and quantifying a fluorescent signal of said fluorophore thereby quantifying the NTBI in the biological sample.

As used herein the phrase "free iron levels" refers to non-transferrin bound iron (i.e., NTBI).

As used herein the term "NTBI" refers to directly chelatable iron (DCI) which is accessible to exogenous iron chelators; mobilizer-dependent chelatable iron (MDCI) which is accessible to exogenous iron chelators upon addition of mobilizing agents; and labile plasma iron (LPI) including redox active iron, which redox activity is eliminated upon addition of exogenous iron chelators.

As used herein the term "labile plasma iron (LPI)" refers to the fraction of the NTBI which is redox active and chelatable.

The term "enhanced labile plasma iron (eLPI)" refers to the redox active iron component following mobilization with NTA at the indicated concentrations. eLPI and NTBI are interchangeably used herein.

Redox active iron [i.e., ferrous iron] is highly damaging when labile [Herbert (1994) Stem Cells 92:1502-1509]. Ferric iron [i.e., Fe(III)] is a relatively nontoxic form of iron. However, ferrous iron [i.e., Fe(II)] plays a significant role in the generation of oxygen species (ROS), excess of which has been proven to be extremely harmful to the health of individuals. Free radical toxicity is produced primarily by the hydroxy radical (.OH). Most of the —OH generated in vivo comes from iron-dependent reduction of $H_2O_2$ [Halliwel (1986) Archi. Biochem. Biophys. 46:501-14]. It is well established that redox active iron and its reaction products (i.e., ROS) promote numerous diseases including cancer, diabetes, heart diseases and liver diseases [Haliwell, B. and Guterridge, J. M. (1995). Role of free radicals and catalytic metal ions in Human Disease: An overview. Meth. Enzymol 186:1-85].

Accordingly, it is essential to quantify redox active iron in a biological fluid.

The phrase "biological fluid" refers to a biological fluid such as blood, serum, plasma, lymph, bile fluid, urine, saliva, sputum, synovial fluid, semen, tears, cerebrospinal fluid, bronchioalveolar large fluid, ascites fluid, pus and the like. The sample may be free of cells or comprise cells.

According to a specific embodiment of the invention, a specific run of the assay measures a single type of a biological fluid (e.g., serum, blood or plasma), while implementing the assay on separate replicate samples (biological samples) of the biological fluid. Thus, for instance, duplicate or triplicate biological samples of the biological fluid can be analyzed in the NTBI or LPI assay.

It will be appreciated that serum and plasma provide similar results.

Thus, a sample of the biological fluid is contacted with a reducing agent to obtain redox-active iron. . The reducing agent is selected capable of reducing free iron from ferric to ferrous form. Suitable reducing agents according to this aspect of the present invention include, but are not limited to, ascorbic acid, dithionite, mercaptoacetic acid, dithiothreitol.

Preferably, a physiological concentration of ascorbic acid is used according to this aspect of the present invention.

Reduced iron is capable of reacting with any oxygen species dissolved in the sample to generate redox active iron reaction products (e.g., ROS).

Thereafter, the reduced sample is contacted with a nitrilotriacetate (NTA) at a concentration of 0.4-2 mM (e.g., 0.4-1 mM, 0.5-1.9 mM, 0.6-1.8 mM, 0.7-1.7 mM, 0.8-1.6 mM, 0.9-1.5 mM, 1-1.4 mM, 1.1-1.3 mM, 0.4-1.5 mM, 0.5-1 mM, 0.5-1.5 mM or 1-2 mM), to mobilize non-transferrin bound iron including redox inactive and the redox active iron in the sample. It will be appreciated that the biological sample can be incubated simultaneously with both the NTA and the reducing agent.

Another embodiment of the method of this aspect of the present invention may include the exclusion of endogenous apo-transferrin and/or iron free transferrin from the sample prior to free iron determination.

Apo-transferrin is universally found in human sera, except in cases of extreme iron-overload where the transferrin is 100% iron-saturated. Therefore the detection of free iron may be rendered more difficult once the sample contains nearly normal levels of apo-Transferrin. The use of Fl-aTF as a probe equalizes the probability that the mobilized iron will bind to the indicator molecule or to endogenous apo-Transferrin in the sample.

Exclusion of endogenous apo-transferrin can be effected by incubating (i.e., pre-clearing) the sample with anti-apo-transferrin antibodies, such as solid phase coupled anti-transferrin antibodies available from Pharmacia, Uppsala and Bio-Rad Laboratories, Hercules, Calif. Additionally or alternatively anionic beads such as MacroPrep® High S support beads available from Bio-Rad Laboratories, Hercules, Calif. can be used to exclude apo-transferrin from the sample.

Preferably, exclusion of apo-transferrin is effected by co-incubating the sample with an apo-transferrin binding metal other than iron such as Gallium and Cobalt. These metals mimic iron and bind to the indicator molecule of the present invention, preventing their reaction with iron [Breuer and Cabantchik Analytical Biochemistry 299, 194-202 (2001)].

However, when using such metals, measures are taken not to use indicator molecules which are affected by such metals. Hence, a preferably used indicator molecule is Fl-aTf, described hereinabove, which is not affected by Gallium due to a biochemical mechanism which is yet to be determined. This apparent insensitivity to Gallium gives the Fl-aTf indicator an iron-binding advantage over the endogenous Apo-transferrin, overcoming most of its interference.

Mobilized and reducer-treated sample is then contacted with an indicator (detector) molecule, which can be measurably activated upon interaction with the newly generated mobilized redox active iron reaction product.

Finally, activation of the detection molecule is quantified, thereby quantifying redox active iron levels in the biological fluid.

The iron indicator is typically comprised of an iron binding moiety and a signal generating moiety, wherein an intensity of the signal generated by the signal generating moiety is related to an amount of the iron bound by the iron binding moiety. The iron binding moiety and the signal generating moiety might be contiguous in the same molecule (i.e., covalently attached to form a single molecule) or distinct molecules bound on separate, but proximal, sites of a polymer or a multimer such as a dendrimer (PCT/IL2012/050119 and WO2004/040252) each of which is incorporated herein by reference provide ample examples of such molecules and methods of using same).

The phrase "iron binding moiety" refers to an iron chelator, which binds to or combines with iron ions, including all synthetic and natural organic compounds known to bind iron, and any molecule of biological origin, or by-product or modified product of a molecule of biological origin, such as proteins, sugars or carbohydrates, lipids and nucleic acids, and any combination thereof, that may bind iron ions.

Examples of iron binding proteins include but are not limited to transferrin, apo-transferrin, lactoferrin, ovotransferrin, p97-melanotransferrin, ferritin, Ferric uptake repressor (FUR) proteins, calcineurin, acid phosphatase and ferredoxin.

According to a specific embodiment, the iron binding moiety is transferrin (Tf), since iron binding to Tf or apo-Tf is significantly faster than to other known iron binding molecules, which enhances the probability that free iron (including NTBI) will bind the indicator molecule rather than to endogenous apo-Tf.

Chemical moieties which are suitable for use as the iron binding moiety of this aspect of the present invention include iron chelators. The phrase "an iron chelator" refers to a molecule comprising nonmetal atoms, two or more of which atoms are capable of linking or binding with an iron ion to form a heterocyclic ring including the metal ion.

Examples of iron chelators include but are not limited to desferrioxamine (DFO), Deferoxamine, Deferiprone, Deferasirox, FBS0701 (Shire Pharmaceuticals) phenanthroline, ethylene diamine tetra-acetic acid (EDTA), diethylene triamine-pentaacetic acid (DTPA), N,N'-bis[2-hydroxybenzoyl]ethylene diamine-N,N'-diacetic acid (HBED) and the like. Other examples of iron chelators and related compounds are provided in U.S. Pat. Nos. 4,840,958, 5,480,894 4,585,780, 5,925,318 and in Hider (1996) Acta Heamatologica 95:6-12.

The signal generating moiety of the indicator molecule, described herein above, is selected such that the intensity of signal generated therefrom is related to the amount of the iron which is bound to the iron binding moiety. According to a specific embodiment, the intensity of the signal is stoichiometrically related to the iron bound by the iron binding moiety.

One of the properties of ionic iron is its inherent ability to affect the fluorescence properties of fluorophores when in atomic or molecular contact, usually resulting in the quenching of the fluorescence signal [Lakowicz, J. R. (1983) Principles of fluorescence spectroscopy, Plenum Press, New York, pp. 266 ff.]. Hence, according to a specific embodiment, the signal generating moiety is a fluorophore, which can be quantified via its fluorescence, which is generated upon the application of a suitable excitatory light. The use of a fluorophore as the signal generating moiety allows the generation of a direct correlation between changes in fluorescence and NTBI concentration. According to some embodiments of the invention, the fluorophores are selected fluorescent in most channels of a flow-cytometer or a fluorometer.

A non limiting list of commercially available fluorophores suitable for use as the signal generating moiety of the present invention along with approximate absorption (Abs) and fluorescence emission (Em) is provided in Table 1 below. The listed fluorophores are available from Molecular Probes.

TABLE 1

| Fluorophore | Fluorescence color (Abs/Em) |
| --- | --- |
| Alexa Fluor 350 | Blue (346/442) |
| Marina Blue | Blue (365/460) |
| Pacific Blue | Blue (410/455) |
| Alexa Fluor 430 | Yellow-Green (433/539) |
| Fluorescein-EX | Green (494/518) |
| CALCEIN | Green (485/517) |
| Alexa Fluor 488 | Green (495/519) |
| Oregon Green 488 | Green (496/524) |
| Oregon Green 514 | Green (511/530) |
| Alexa-Fluor 532 | Yellow (532/554) |
| Alexa-Fluor 546 | Orange (556/573) |
| Tetramethylrhodamine | Red-Orange (555/580) |
| Rhodamine Red-X | Red-Orange (570/590) |
| Alexa Fluor 568 | Red-Orange (578/603) |
| Texas Red-X | Red (595/615) |
| Lucifer Yellow | 425/531 |
| BODIPY TMR | 544/570 |
| BODIPY 493/503 | 493/503 |
| BODIPY 499/508 | 499/508 |
| BODIPY 507/515 | 507/515 |
| NBD | 478/541 |
| Sulforhodamine | 555/580 |

Alternatively, a fluorophore can be a protein belonging to the green fluorescent protein family including but not limited to the green fluorescent protein, the yellow fluorescent protein, the cyan fluorescent protein and the red fluorescent protein as well as their enhanced derivatives.

Optionally, the signal generating moiety of the indicator molecule can be an enzyme which when in the presence of a suitable substrate generates chromogenic products. Such enzymes include but are not limited to alkaline phosphatase, β-galactosidase, β-D-glucoronidase and the like.

It will be appreciated that a naturally occurring molecule such as an enzyme can comprise the indicator molecule of the present invention, wherein following iron binding a measurable conformational and/or a functional alteration is affected. For example, the aconitase enzyme is activated following iron binding [Klausner, R. D. et al. (1993) Cell 72:19-28].

According to a specific embodiment of this aspect of the present invention the indicator molecule is DFO e.g., fluoresceinated deferrioxamine (Fl-DFO).

According to a specific embodiment of this aspect of the present invention the indicator molecule is 5-4,6-dichlorotriazinyl aminofluorescein (DCTF)-apo-transferrin i.e., Fl-aTf.

According to a specific embodiment, the iron indicators are selected from the group consisting of calcein, deferiprone, deferasirox (Exjade) and salicyl-aldehyde hydrazone (SIH).

The indicator molecules of the present invention can be synthesized using well known chemical synthesis procedures. Detailed protocols describing how to use reactive fluorophores are available in Molecular Probes.

For example, amine-reactive fluorophores (i.e., including a reactive group such as dichlorotriazinyl, isothiocyanate, succinimidyl ester, sulfonyl chloride and the like) can be used to modify proteins, peptides and various synthetic molecules with primary amines.

Following conjugation, unconjugated fluorophore is removed, usually by gel filtration, dialysis, HPLC or a combination of these techniques. The presence of free fluorophore, particularly if it remains chemically reactive, can greatly complicate subsequent analysis with the indicator of the present invention.

According to a specific embodiment, the indicator molecules of the invention are characterized by a high fluorescence yield yet retain the critical parameters of the unlabeled iron binding moiety (i.e., iron binding).

It will be appreciated though, that oftentimes, highly labeled conjugates are likely to precipitate or bind nonspecifically. It may therefore be necessary to have a less-than-maximal fluorescence yield to preserve function or binding specificity.

As described herein above, the indicator molecule of the present invention can be a chimeric protein including a protein fluorophore (e.g., GFP) linked to an iron binding protein. Such a chimeric protein can be produced via well known recombinant techniques.

It will be further appreciated that commercially available indicator molecules can also be used according to this aspect of the present invention. For example, calceins are commercially available from Molecular Probes Inc, FL-DFO, synthesized by reacting FITC with desferrioxamine (available from Evrogen, Moscow, Russian Republic) and the respective isothiocyanate derivatives of DFO (DFO-ITC) and DTPA (DTPA -ITC) are obtainable from Macrocyclics Inc (Dallas, Tex., USA), RITC and derivatives are available from Fluka (Sigma-Aldrich Co., St. Louis, Mo., USA).

According to a specific embodiment, the molecule comprises DFO.

According to a specific embodiment, the iron indicator comprises dihydrorhodamine 123 (DHR) or carboxydihydrofluorescein (CDCF).

According to a specific embodiment, the iron indicator comprises calcein.

According to a specific embodiment, the molecule comprises a modified apo-transferrin.

According to a specific embodiment, the molecule comprises fluorescein-apo-transferrin.

According to a specific embodiment, the fluorophore is selected from the group consisting of Fluorescein, Rhodamine, nitrobenzfurazan, fluorogenic β-galactosidase and a green fluorescent protein.

According to a specific embodiment the fluorophore is dihydrorhodamine-123 (DHR), which converts to fluorescent rhodamine, dichloro-dihydrofluorescein, which converts to dichlorofluorescein, dihydroresorufin which converts to resorufin and the like.

Detecting and quantifying the fluorescent signal of the fluorophore may be affected using any method which is known in the art. For instance, using fluorescence activated cell sorter (FACS) or a fluorescence plate reader. Methods of measuring using a fluorescence plate reader are described in length in WO2004/040252.

In order to measure by FACS the indicator is first conjugated to a microparticle.

As used herein the term "microparticles" or "beads" refers to particles having a mean diameter 0.1 to 100 μm (e.g., 5-10 μm). Microparticles have a much larger surface-to-volume ratio than at the macroscale, rendering the compositions of the invention highly advantageous in terms of affinity to free iron.

According to a specific embodiment, the microparticles comprise microspheres.

The microparticle should preferably be made of such material and be of such size as to stay suspended, with minimal agitation if necessary, in solution or suspension (i.e., once the sample is added). It should preferably not settle any faster than cells of interest in the sample, as further described herein below. The material from which the microparticles are made should be such as to avoid clumping or aggregation, i.e., the formation of doublets, triplets, quadruplets and other multiplets. This can be minimized by using mild detergents such as Triton X-100 (0.05%).

Microparticles may be used in accordance with the present teachings include, but are not limited to fixed human red blood cells, coumarin beads, liposomes, cell nuclei and microorganisms. However, particularly advantageous examples of microparticles that may be used in the invention include microbeads, such as agarose beads, polyacrylamide beads, polystyrene beads and silica gel beads.

Other microparticles for use in the methods and compositions described here include plastic microbeads. While plastic microbeads are usually solid, they may also be hollow inside and could be vesicles and other microcarriers. They do not have to be perfect spheres in order to function in the methods described here. Plastic materials such as polystyrene, polyacrylamide and other latex materials may be employed for fabricating the beads, but other plastic materials such as polyvinyl chloride, polypropylene and the like may also be used. According to a specific embodiment, the microparticles are polystyrene beads, silica beads or agarose beads.

According to a specific embodiment, the microparticle has a molecular size of 4-10 μm similar to, or lower than most mammalian cells.

The significance of using analytical beads of sizes similar to those of mammalian cells is first because beads must have >2-3 μm diameter for proper flow cytometry (FC) analysis; and second for obtaining changes in fluorescence intensity per particle/cell under equivalent conditions.

Thus, the indicator molecules coat the microparticles. Preferably, the coating is homogeneous. Attachment or conjugation of the indicator molecule to the microparticle is effected such that the functionality of the indicator molecule is unharmed (that is, without compromising neither the signal intensity nor the binding to the metal binding moiety). Chemistries for conjugating the indicator to the microparticles are described in IL2012/050119.

The assays described herein are performed in reference to control samples in which the concentration of free iron is known. In specific embodiments, a calibration curve is generated so as to accurately quantify the concentration of the iron in the sample.

While further reducing the present invention to practice, the present inventors have realized that determining the level of eLPI (NTBI) may be performed along with an independent determination of LPI.

For example, as described in Examples 7 and 8, measuring LPI and eLPI is shown to be important for determining patient's compliance to treatment and in order to better determine patient's NTBI levels prior to the initiation of any therapy or following treatment in order to determine treatment's efficacy.

Thus, according to an aspect of the invention there is provided a method of quantifying free iron levels in a biological fluid of a subject in need thereof, the method comprising:

(a) analyzing labile plasma iron (LPI) in a first biological sample of the biological fluid of the subject; and (b) analyzing NTBI in a second biological sample of the biological fluid of the subject, thereby quantifying free iron levels in the biological fluid of the subject.

Such a method can be implemented also in personalized treatment protocols in order to determine treatment regimen.

Thus there is provided a method of treating a subject having a disorder associated with abnormal levels of free iron in a biological fluid, the method comprising:

(i) quantifying free iron levels (NTBI and optionally LPI) in a biological fluid of the subject according to the method described herein; and (ii) treating the subject with a chelation therapy.

Each of the quantification steps i.e., NTBI, LPI or both can be effected prior to or following treatment.

For example, quantifying NTBI (i)(b) is affected prior to treatment and quantifying LPI (i) (a) is effected following treatment (ii).

Alternatively, quantifying LPI (i)(a) is effected concomitantly with NTBI (i)(b).

The measurement of NTBI is described in length hereinabove. Determination of LPI is similarly performed, only no mobilization with the indicated NTA levels is affected.

Thus, for instance, a subject, in need thereof, is firstly analyzed for NTBI prior to the initiation of any treatment, for instance in subjects suspected as having, or at risk of a disorder associated with abnormal levels of free iron. This is typically performed at childhood. Thereafter, LPI level is determined relatively immediately following treatment (e.g., typically less than 24 hours following treatment with a chelation treatment). Alternatively, both LPI and NTBI are determined each time (on separate biological samples of the biological fluid).

Thus, the present teachings can be used in diagnosis of medical conditions (disorders) associated with abnormal free iron levels.

Thus, there is provided a method of determining a presence, absence or risk of a disorder associated with abnormal levels of free iron in a biological fluid of a subject, the method comprising:

(a) determining levels of the free iron in the biological fluid of the subject according to any of the methods described herein (LPI, eLPI or both); and (b) determining in the subject based on said levels a presence, absence or risk of the disorder associated with abnormal free iron levels.

As used herein the term "diagnosis" or "diagnosing" refers to determining presence or absence of a pathology (e.g., a disease, disorder, condition or syndrome associated with abnormal levels of free iron in a biological fluid or cells), classifying a pathology or a symptom, determining a severity of the pathology, monitoring pathology progression, forecasting an outcome of a pathology and/or prospects of recovery, determining a risk for the pathology and screening of a subject for the pathology.

Examples of disorders and conditions which are associated with abnormal levels of free iron include, but are not limited to, hemolytic diseases hemoglobinopathies, thalassemia, thalassemia major, anemia, sickle cell anemia, aplastic anemia, megaloblastic anemia, myelodyplasia, diseases which require repeated transfusions, diseases which require dialysis, hereditary hemachromatosis, cancer, heart diseases, Myelo Dysplasia Syndrome (MDS), iron poisoning and rheumatoid arthritis.

Once the assay is performed, the results are recorded. A physician or a lab technician classifies the subject as having, predisposed to, or free-of the disorder and informs the results to the subject.

Diagnosis may be substantiated using other methods which are well known in the art. For instance, complete blood count, ferritin and related tests such as hemoglobin and mean corpuscular volume.

Once diagnosis is made, the subject may be treated with appropriate therapy.

Thus, according to an aspect of the invention there is provided a method of treating a subject having a disorder associated with abnormal levels of free iron in a biological fluid, the method comprising:

(i) quantifying free iron levels in a biological fluid of the subject according to the methods described herein (i.e., eLPI, LPI or both); and (ii) treating the subject with a chelation therapy.

When quantifying (i) is performed prior to treating (ii), the present teachings are typically performed in order to determine the treatment regimen.

Alternatively, quantifying (i) is effected following treating (ii), in which case the present teachings are performed in order to determine the efficacy of treatment. Reduced levels of LPI, eLPI or both following treatment are indicative of an efficacious treatment.

According to another embodiment, quantifying (i) is effected prior to treating (ii) and following treating (ii). In such a case the present teachings relate to determining the treatment regimen and following its success.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., a damage to healthy cells or tissue). The type of treatment can include a blood transfusion or chelation therapy or any other therapies used in the present field. The dosage, schedule and duration of treatment can vary, depending on the severity of pathology and the selected type of treatment, and those of skills in the art are capable of adjusting the type of treatment with the dosage, schedule and duration of treatment.

As used herein "chelation therapy" refers to the administration of chelating agents to remove free iron from the body. Examples of chelating agents include, but are not limited to desferrioxamine, Deferiprone, Deferasirox, FBS0701, phenanthroline, ethylene diamine tetra-acetic acid (EDTA), diethylene triamine-pentaacetic acid (DTPA) and N,N'-bis[2-hydroxybenzoyl]ethylene diamine-N,N'-diacetic acid (HBED).

As used herein "subject in need thereof" includes mammals, preferably human beings at any age which suffer from the pathology. According to a specific embodiment, this term encompasses individuals who are at risk to develop the pathology or who have already been diagnosed with the pathology. The subject may be an infant or a child (i.e., 10 years or younger), an adolescent (e.g., 11-18) or an adult (e.g., >18).

The present teachings can also be harnessed in favor of identifying subject's compliance i.e., the degree to which a patient correctly follows medical advice. In this case, adherence to chelation therapy.

Figure 5:
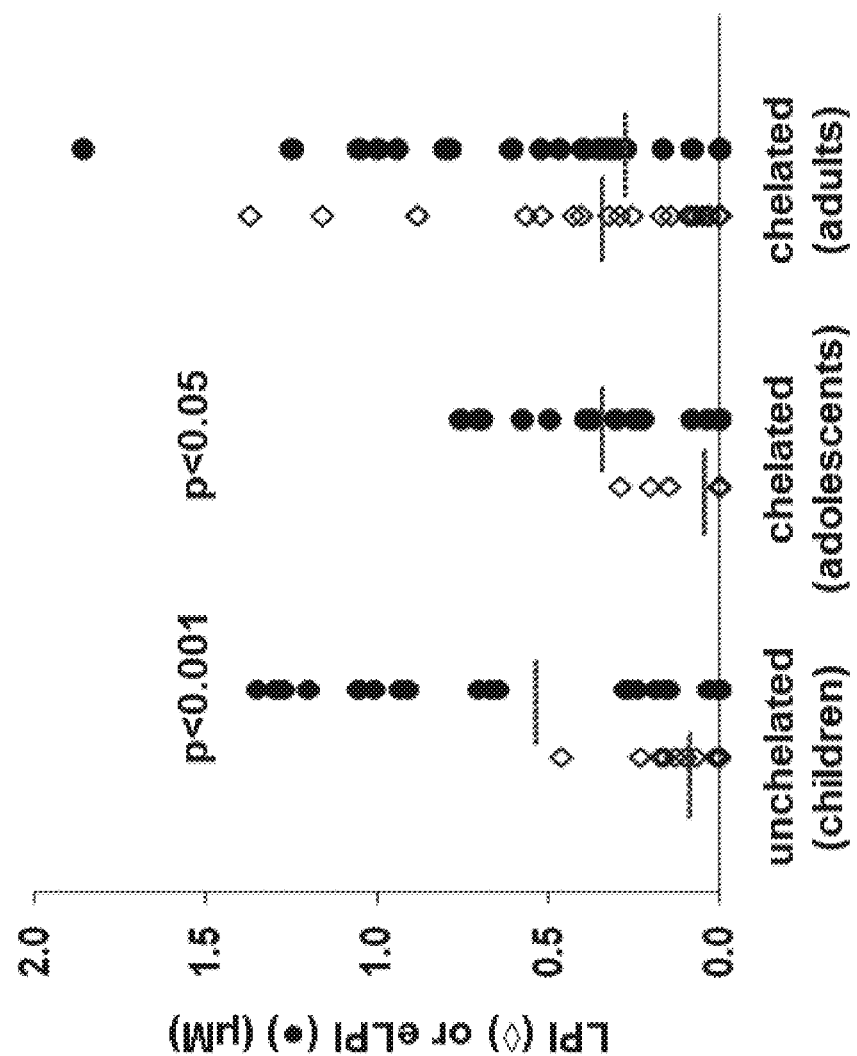
FIG. 5 is a graph showing a comparison between LPI and eLPI values in three different groups of thalassemia patients. The individual values of LPI (open diamond) and eLPI (closed diamond) are plotted against patient age and chelation group and the median indicated by the dotted line. The patient groups were non-chelated children (3-13 yrs, European Hospital in Gaza, Palestine; EGH), chelated adolescents/young adults (14-30 yrs, Haemek Medical Center, Afula, Israel; HMCA) and chelated adults (31-61 yrs, Hadassah Medical Center, Jerusalem, Israel; HMCJ). Patients whose ages did not fit the age category assigned to their medical center were excluded. P values were calculated by ANOVA parametric test indicating significant difference between LPI and eLPI.

The levels of LPI and eLPI are affected by the treatment regimen. A subject who has never been treated with chelator therapy, will exhibit significantly higher levels of eLPI as compared to LPI (see FIG. 5).

On the other hand, measurement of eLPI and LPI for subjects not treated with chelation therapy for over 24 hours will result in similar results i.e., LPI=eLPI. However, measurement of LPI and eLPI immediately after administration of the chelator (e.g., 2-24 hours) will show basal level of LPI i.e., close to zero, but NTBI (eLPI) may increase.

Therefore, not only can the present teachings be used for diagnosis and determining treatment efficacy but also patient's compliance.

Thus, according to an aspect of the invention there is provided a method of determining subject's compliance to chelation therapy, the method comprising:

(a) retrieving a biological fluid of a subject in need thereof 2-24 hours following alleged administration of the chelation therapy; and (b) quantifying, in the biological fluid of the subject, free iron levels including LPI and NTBI, as described above. An increase in NTBI level compared to LPI level is indicative of subject's compliance (i.e., the subject follows the medical instructions for chelation therapy). Conversely, the same LPI and NTBI levels (e.g., both provide a positive or negative iron levels) are indicative of non-compliance.

As used herein "alleged administration" refers to self-administration based on subject's statement.

According to a further aspect of the invention there is provided a method of determining efficacy of treatment of a disorder associated with abnormal levels of free iron in a biological fluid, the method comprising:

(a) treating a subject in need thereof using a medicament for the disorder associated with abnormal free iron levels; and (b) determining levels of said free iron in a biological fluid or cells of said subject according to any of the methods described herein (NTBI, LPI or both), wherein a change in said levels following the treating is indicative of treatment efficacy.

According to a specific embodiment, the medicament comprises iron chelation therapy, and whereas a reduction in the levels following said therapy is indicative of efficacious treatment.

Examples of disorders and conditions which are associated with abnormal levels of free iron include, but are not limited to, hemolytic diseases hemoglobinopathies, thalassemia, thalassemia major, anemia, sickle cell anemia, aplastic anemia, megaloblastic anemia, myelodyplasia, diseases which require repeated transfusions, transplantation (e.g., bone marrow), diseases which require dialysis, hereditary hemachromatosis, cancer, heart diseases, Myelo Dysplasia Syndrome (MDS), iron poisoning, diabetes, end-stage kidney disease and rheumatoid arthritis.

According to a specific embodiment, the subject has or is diagnosed with thalassemia.

Compositions of some embodiments of the invention may, if desired, be presented in a pack or dispenser device, such as an FDA approved kit, which may contain one or more components for performing the present assays. For example, the kit may comprise in separate containers, the NTA for use at the indicated concentration, the indicator and possibly the reducing agent. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5 and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Experimental Procedures

Materials. Nitrilotriacetate (NTA), NaCl, Hepes (N-2-hydroxyethylpiperazine-N-2-ethanesulfonic acid), human serum albumin Fraction V; ferrous ammonium sulfate (FAS), sodium citrate, uric acid, deferrioxamine (DFO) were from Sigma-Aldrich, St. Louis Mo. Human apo-Tf was from Kamada Ltd. (Beit-Kama, Israel). Dihydrorhodamine 123 was from Biotium Inc. (Hayward, Calif.), deferiprone (DFP, 1,2-dimethyl-3-hydroxypyridin-4-one=Ferriprox™) from Apo-Pharma (Toronto, ON), DFR (Deferasirox=Exjade™) and DFO (Deferrioxamine™ from Novartis-Pharma (Basel, Switzerland).

Preparation of iron:citrate and iron:NTA. The complexes Fe:citrate and Fe:NTA were generated by dissolving dry FAS in 10 mM Na-citrate or Na-NTA pH 7.0 solutions to produce an Fe:ligand ratio of 1:10. The solutions were allowed to stand for more than 24 hrs to allow oxidation of Fe(II)>Fe(III) before use.

Preparation of iron-saturated human Tf. Human apo-Tf 16 mg/ml in 20 mM Hepes pH 7.4 containing 20 mM $NaCO_3$ was supplemented at 5 mM intervals with fresh 0.45 mM FAS under mixing to produce 1:2.2 apo-Tf: Fe complexes. Following 10 mM incubation, 0.5 mM DFO was added to scavenge NTBI iron and after 20 min the solution exhaustively dialyzed against 150 mM NaCl.

Preparation of iron-free human serum albumin. A solution of 20 mg/ml human serum albumin Fraction V in 0.15 M NaCl supplemented with 0.8 mM DFO was exhaustively dialyzed against 0.15 M NaCl.

Patients. Poly-transfused thalassemia major and intermedia (all transfusion-dependent) patients from 3 medical centers: 1. European Hospital in Gaza (EHG), where the patients (n=30; ages 3-13, serum ferritin 1200-7100 ng/ml, transferrin saturation 65-100%) are regularly transfused, but only sporadically chelated, having received no chelation for at least 3 months prior to this study. Most (70%) thalassemia major patients at EHG are homozygous for mutation IVS1:110 or IVS1:1. 3. Haemek Medical Center (HMCA) (Afulah, Israel) where the patients (n=29, ages 6-28, serum ferritin 740-7900 ng/ml, transferrin saturation 74-132%) are under regular transfusion/chelation treatment and come from variable ethnic backgrounds with various β-globin mutations (26 were thalassemia major of which 13 were homozygous for mutation IVS1:110). The majority (85%) of the HMCA patients were treated for the last 2 years with DFR. 3. At Hadassah Medical Center in Jerusalem (HMCJ), the patients (n=26, ages 27-61, serum ferritin 1000-6000 ng/ml, transferrin saturation >75%) were from various ethnic backgrounds carrying different β-globin mutations, all under regular transfusion/chelation treatment (40% on DFR, 30% on DFO in combination with DFP and 30% on DFP). Patients provided written consent for blood taken for the assessment of serum iron and/or oxidative stress parameters, as part of their ongoing maintenance treatments, as approved by the respective institution review boards (IRBs) and for children, ratified by the Ministry of Health. Blood samples were taken 14±5 days after last transfusion and (where applicable) patients were instructed not to take medication in the day of blood withdrawal, as approved by the hospital IRB. Serum samples were aliquoted and kept frozen at −15° C. for up to 1 month prior to iron determination, and their freezing and thawing was restricted to no more than 2 times. For long term preservation the samples were kept at −80° C.

Determination of LPI and DCI. The properties of the assays used in this study in their different modalities are compiled in Table 2, below.

TABLE 2

| Name of assay | Mobilizing agent | Detection mechanism | Parameter detected | Probe detector | Analytical instrument |
|---|---|---|---|---|---|
| LPI 17,18 | None | Ascorbate/Fe prompted ROS formation | Chelator blockable rise of fluorescence | DHR | Plate reader or fluorimeter |
| eLPI | NTA (0.5 mM) | Ascorbate/Fe prompted ROS formation | Chelator blockable rise of fluorescence | DHR | Plate reader or fluorimeter |
| DCI 19 | None | Fe binding to chelator | Quenching of fluorescence | Fluorescein-DFO | Plate reader or fluorimeter |
| eDCI | NTA (0.1 mM) | Fe binding to chelator | Quenching of fluorescence | Fluorescein-DFO | Plate reader or fluorimeter |

LPI determination, The LPI (Labile iron in plasma) assay was used as described previously [17,18] or in the presence of NTA added from a concentrated solution. In experiments testing the effects of various additives on LPI, 20 µl of the additives dissolved in HBS (HEPES buffered saline composed of 20 mM HEPES, 150 mM NaCl, pH 7.4) were mixed with 20 µl of serum. Control samples and iron standards were similarly diluted with HBS. LPI assays without added NTA ('redox-active LPI') are designated "LPI" and LPI assays with added NTA (0.5 mM unless stated otherwise) are designated "eLPI".

Although in this study only serum samples were used while using the term LPI that denotes 'labile plasma iron', the present inventors have previously shown that LPI values are identical in plasma and serum samples from the same individual [17].

DCI determination. The DCI assay (directly chelatable iron) was used for sample analysis of labile iron by assessing its binding to fluorescein-DFO (Table 1) with a fluorescence plate reader [19] or adapted for flow cytometry using as analytical probe fluorescein and DFO covalently coupled to chemically modified polystyrene beads (Spherotec Inc., Lake Forest, Ill., USA) (and an Eclipse instrument (iCyt, Champaign, Ill., USA) (Breuer et al, to be published elsewhere). In tests of the effect of NTA on DCI determination, NTA was added from a stock solution directly to the assay reagents. In experiments testing the effects of various additives on DCI, 20 µl of the additives dissolved in HBS were mixed with 20 µl of serum samples and the combined mixture (40 µl) was used in the assay. Control samples and iron standards were similarly diluted with HBS. In previous publications the term DCI has always indicated the assay format without NTA. In the present work the two formats of the DCI assay are designated DCI (−) (without NTA) and DCI (+) (with 0.1 mM NTA).

Example 2

Rationale of the Study

Measurements of LPI were originally designed for the detection of labile forms of iron in native human plasma or serum [17]. The purpose was to assess if those labile forms could serve as indicators of impending tissue iron overload and as direct targets of chelation, on the basis that they should be comprised of chemical forms that are distinguishable from the non-labile Tf-bound iron in that they are redox-active, exchangeable with other ligands and accessible to chelators. This led to simple and sensitive assays that are performed under nearly physiological conditions, with 40 µM ascorbate added to initiate redox cycling of the iron and ensuing generation of reactive oxygen species (ROS) that are quantified by a fluorescence assay (Table 1). Furthermore, unlike other studies [11,14,15], the LPI assay does not depend on supplementation of strong iron-mobilizing agents, or high affinity chelators [16,20]. Thus, the assay avoids the inadvertent detection of transferrin-bound iron [15] or labile iron-chelates [19,21-23]. The detected LPI reflects the most labile or redox-active forms of NTBI in native plasma or serum, but not putative forms bound to non-labile ligands (e.g. citrate, albumin) In addition, the detection of LPI might be susceptible to masking by plasma antioxidants. In order to differentiate between the redox-active fraction and total NTBI in a single assay system, the present inventors tested the possibility that adding low concentrations of a mobilizing agent to the LPI assay could serve as a means of revealing the total serum NTBI content. For comparison, they also used a more direct assay for NTBI, in which DFO-chelatable iron is determined by its stoichiometric binding to the probe fluorescein-DFO in the presence and absence of an iron mobilizing agent.

Example 3

Effect of Nitrilotriacetate on the LPI Assay

As the iron-mobilizing effect of NTA on NTBI has been previously shown to be dependent on the NTA concentration [14,15], the effect of increasing NTA concentrations on LPI levels in 9 representative sera: 7 from thalassemia patients and 2 from normal individuals (FIG. 1) was assessed. The data indicate that the LPI values increased to various extents with increasing NTA concentrations but attained maxima at concentrations <1 mM NTA. The detected LPI signal reached maximum levels at 0.1 mM NTA in sera with LPI <1 µM and at 0.5 mM NTA in thalassemic sera with LPI >1 µM. Control sera (n=12) remained LPI-negative at all tested concentrations of NTA, a finding corroborated in LPI tests carried out with 0.5 mM NTA on >100 sera from normal individuals (data not shown). The same values of LPI were obtained when sera were assayed with 0.5 mM NTA present in the final assay solution or when sera were preincubated with NTA for 1 hr prior to 10-fold dilution with assay solution lacking NTA. Based on the relatively fast (within minutes) and distinct extraction/mobilization of LPI components by moderate NTA treatment depicted in FIG. 1, a modality of the original LPI assay by incorporating 0.5mM NTA as extracting/mobilizing agent was adopted and referred to as enhanced LPI (eLPI).

Example 4

Effect of Serum Components on LPI and ELPI

Figure 2:
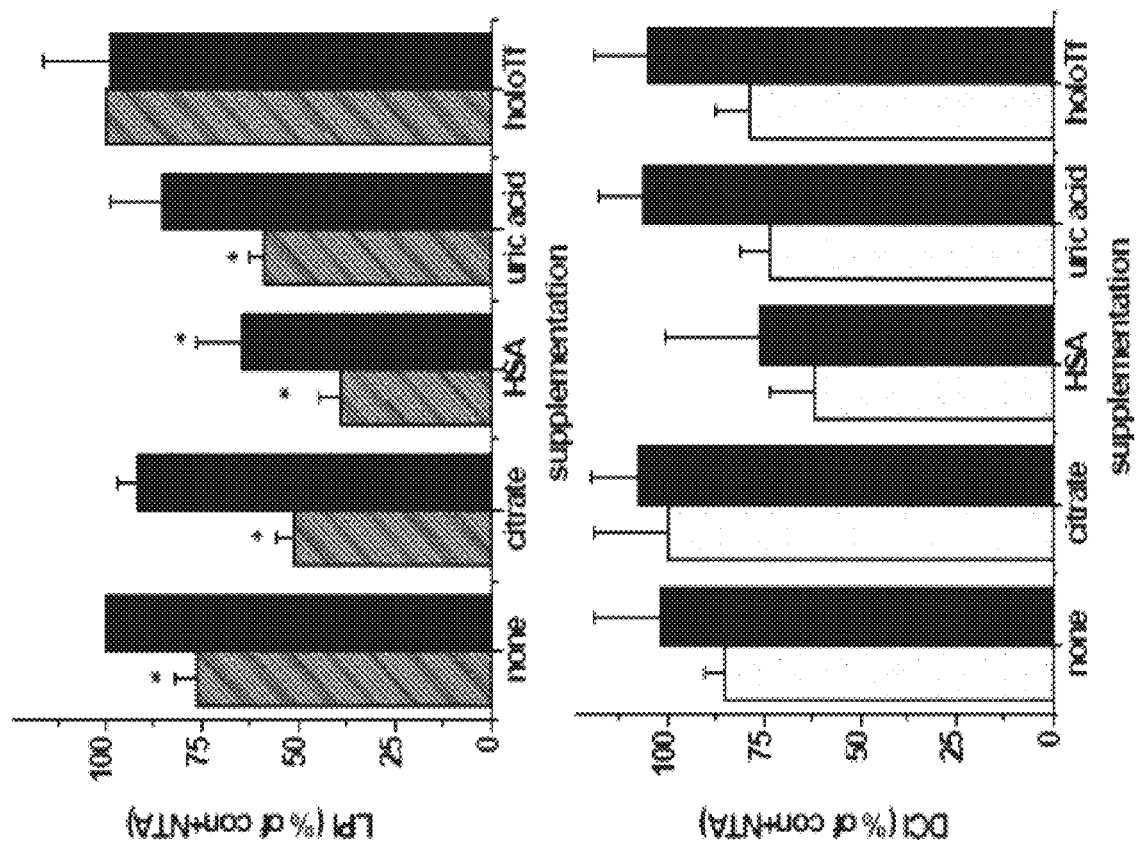
FIG. 2 is a bar graph showing the effect of citrate, human serum albumin, holotransferrin (holoTf) and uric acid on LPI and Directly Chelated Iron (DCI) in thalassemia patient sera assayed with and without NTA. Serum samples (20 µl) were mixed with either HBS (none) or HBS containing either 0.15 mM citrate, 10 mg/ml iron-free human serum albumin, 1 mg/ml of iron-saturated human transferrin or 0.5 mM uric acid. After 15 min incubation, the samples were assayed for LPI (upper panel) or DCI (lower panel) in the absence (white/ crossed columns) or presence of NTA (black columns)" (0.5 mM for LPI and 0.1 mM for DCI). Six adult thalassemia patient sera were used and experiments were run in duplicates. The data are depicted as % of the respective LPI or DCI value obtained in untreated serum with no additions other than NTA ('none') (+NTA) and significant differences ($p<0.05$) from this valueA) are denoted by asterisk *.

Because the LPI assay is performed in essentially native biological conditions, it reflects the weighted effects of the chemical components of that fluid. In plasma or serum, besides unsaturated Tf, the three principal candidate molecules that can affect LPI detection are citrate, as an intermediate-affinity iron ligand that attenuates redox cycling [24], uric acid, as an antioxidant [25] and serum albumin that could function as both [9,26], depending on the level of its oxidation or chemical modification in various disorders [10]. Their respective concentrations in serum of normal individuals are 88-156 µmol/L, 0.16-0.51 mmol/L and 32-45 g/L (=0.48-0.67 mM) [Whole blood, serum and plasma chemistry]. The individual effects of these agents on LPI and eLPI were assessed by adding them at physiological concentrations to sera from 6 thalassemic patients as shown in FIG. 2 (upper panel). Each of the three agents added to thalassemic sera, citrate (0.15 mM), commercially obtained, iron-depleted human serum albumin (10 mg/ml) or uric acid (0.5 mM) significantly attenuated the measured LPI values, but those were efficiently counteracted by NTA in the eLPI assay. To the extent that exogenous addition of the three agents provides an accurate reflection of their LPI-attenuating potential in native plasma, one can conclude that the LPI assay is confined to the detection of overtly labile components of NTBI, whereas eLPI reveals both overtly labile NTBI and significant amounts of masked components of NTBI.

The validity of the above statement regarding LPI and eLPI relies entirely on the condition that applies to all NTBI assays: the presence of transferrin-bound iron must not contribute to the measurements. Since serum Tf concentration is in the range of 2 g/L (~25 µM) and serum iron concentrations often reach 50 µM in iron overload diseases, even a fractional release of Tf-bound iron by mobilizing agents will produce erroneous results in NTBI assays. The present inventors have previously shown that Tf-bound iron does not contribute to LPI [17]. As shown in FIG. 2, adding 1 mg/ml iron-saturated Tf to 6 thalassemia sera in the presence of NTA had no significant effect on eLPI values (confirmed with 8 other LPI/eLPI-positive sera, data not shown), indicating the absence of contribution of iron from Tf to either LPI or eLPI assays.

Example 5

Effect of Serum Components on Directly Chelatable Iron (DCI), an Alternative Measure of NTBI For comparing eLPI with NTBI, the present inventors have employed an alternative assay for NTBI, termed directly-chelatable iron or DCI (FIG. 2, lower panel). Unlike LPI and eLPI which measure iron redox activity, DCI measures the accessibility of NTBI to a fluorescent, high-affinity chelator probe (fluorescein-DFO) [16]. As with measurements of LPI, the DCI signals were also enhanced by NTA in the assay reagent, but to a markedly lower degree than eLPI. This was confirmed by testing 22 TM sera for DCI without and with 0.1 mM NTA. An average increase of 0.14±0.13 µM was obtained in the presence of NTA (Breuer, W. and Cabantchik, Z. I, unpublished observations). The concentration of NTA in the DCI assay had to be limited to 0.1 mM to avoid contributions from holo-Tf-iron. Release of iron from holo-Tf by various carboxylate ligands such as NTA in combination with DFO has been documented previously [27]. Neither citrate nor uric acid significantly affected DCI values, although purified human serum albumin supplemented to sera had an attenuating effect, as in the LPI assay. The present inventors tentatively attribute the exogenous albumin-mediated reduction of DCI to the binding of the fluorescein moiety of fluorescein-DFO to one of purified-albumin's hydrophobic binding sites, leading to a partial loss of sensitivity to quenching of the fluorescent chelator by iron. As the majority of such sites is normally occupied in plasma [28], their interference with the above assay should be minor Example 6

Effect of Chelators on DCI, LPI and eLPI Measurements

Figure 3:
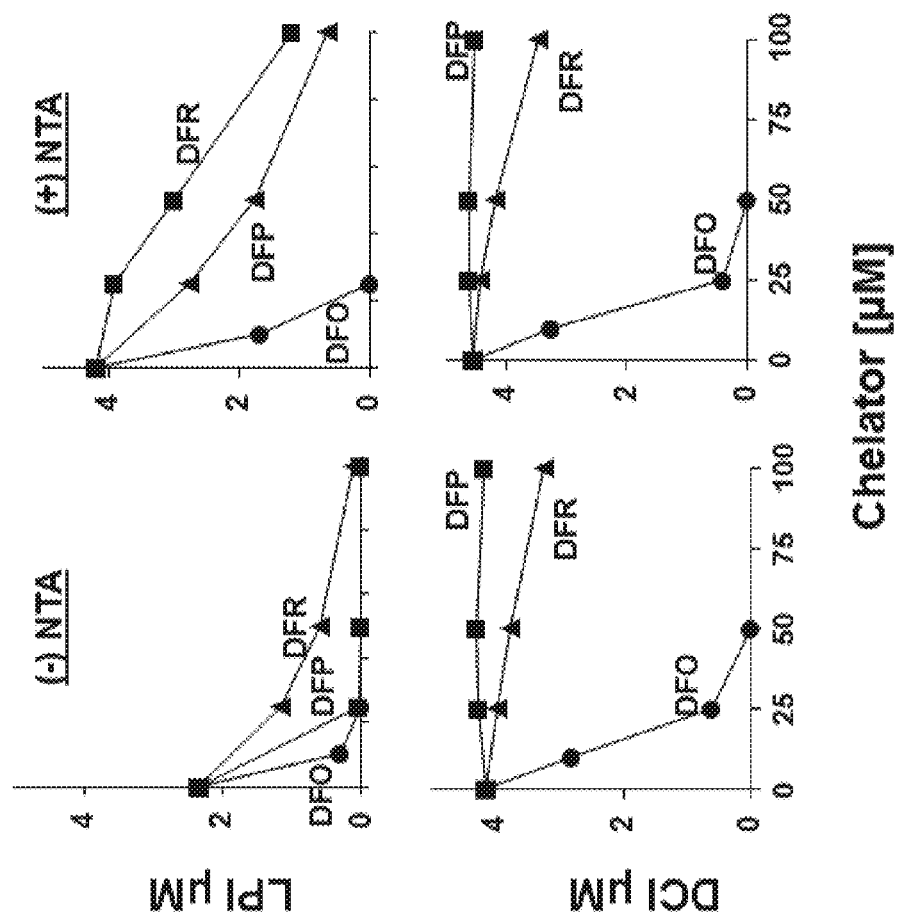
FIG. 3 is a graphic representation showing the effect of chelators in serum on LPI and DCI values without and with NTA (referred to as eLPI and eDCI, respectively). A single mixture of 8 sera from thalassemic children was preincubated for 2 hr at room temperature with increasing concentrations of iron chelators and assayed for LPI (top left panel), LPI (+) NTA (also referred to as eLPI) (top right panel), DCI (bottom left panel) and DCI (+) NTA (also referred to as eDCI) (bottom right panel). The chelators tested were deferiprone, DFP (closed triangle), deferasirox, DFR (closed square) and deferrioxamine, DFO (closed circle) and chelator concentration in the abscissa refers to the final concentration in the serum sample. Qualitatively similar results were obtained in 2 other experiments with different mixtures of sera.

NTBI is considered a primary target of chelators and has been used as an indicator of chelator efficacy [18]. Thus, it was of interest to assess whether the effect of clinically used chelators is comparable between the LPI and eLPI formats, and whether these chelators affect LPI DCI values to a similar extent (FIG. 3). The serum concentration of chelator (2 hr incubation with thalassemia serum at room temperature) required for reducing LPI by 2 µM was <10 µM for DFO and ~25 µM for DFP or DFR. In the eLPI assay these values rose to ~10, 75 and 42 µM respectively. One interpretation of these results is that NTA mobilizes cryptic NTBI forms that are only partially accessible to DFP and DFR, but are chelated by DFO. In contrast to LPI and eLPI, in the DCI assays (without and with NTA) the concentration of DFP and DFR in the serum required to decrease DCI by 2 µM was markedly greater. This is attributable to transfer of chelated NTBI from DFP and DFR to the higher-affinity binding fluorescein-DFO, a previously described phenomenon [22,23,29] that caused underestimation of the effects of DFP and DFR on DCI. Unlike DFP and DFR, DFO competed efficiently with fluorescein-DFO in preventing the detection of DCI.

Example 7

Comparison of Measurement of LPI and eLPI with DCI in Three Different Groups of Thalassemia Patients To test the premise that the eLPI assay detects all NTBI forms, including the redox-active (detected by LPI) and other, redox-inactive NTBI complexes detected in the DCI assay by to the probe fluorescein-DFO, the values obtained by the 3 methods in sera obtained from 3 distinct patient categories were compared. These comprised regularly transfused, iron overloaded thalassemia patients who were either non-chelated children (3-13 yrs, EHG, Group 1), chelated adolescent-young adults (13-2828 years, HMCA, Group 2) and chelated adults (27-61 years, HMCJ, Group 3). The patient groups differ in age, iron overload levels as well as chelation status and their inclusion in the study was largely dictated by accessibility and feasibility constraints. Although this imposes limits on possible comparisons, these disparate groups were suitable for illustrating the applicability of performing both LPI and eLPI measurements in certain patients.

Figure 4:
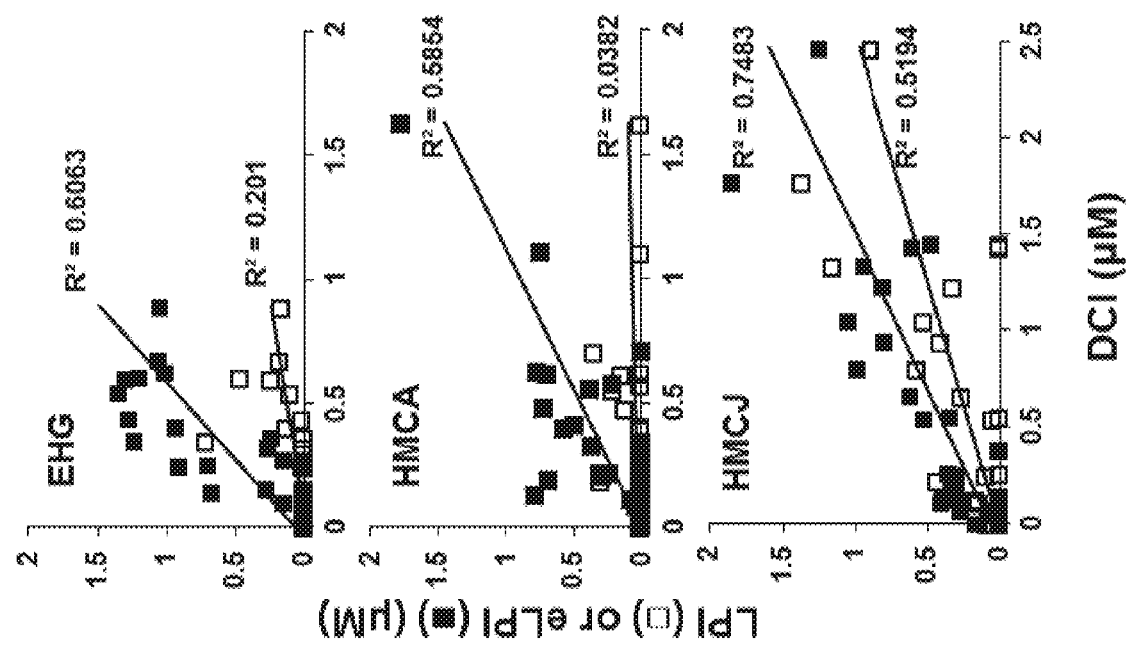
FIG. 4 is a graph showing the correlation between LPI and eLPI vs. DCI in 3 different patient groups. Sera from three groups of regularly transfused, iron overloaded thalassemia patients were tested for LPI, eLPI and DCI. The selected patient groups were restricted to non-chelated children (3-13 yrs, European Hospital in Gaza (EHG), Palestine, top graph), chelated young adults (13-30 yrs, Haemek Medical Center (HMCA), Afula, Israel, middle graph) and chelated adults (27-61 yrs, Hadassah Medical Center (HMCJ), Jerusalem, Israel, bottom graph). Plots of DCI versus LPI (☐) and eLPI (closed square) with trend lines and linear regression values are indicated in the figure for each group.

The percentage of patients with significant DCI levels (≥0.4 µM) in groups 1, 2 and 3 was 32.3, 33.3 and 35.1, respectively. As shown in FIG. 4, a small but significant correlation was obtained between eLPI and DCI in all 3 groups ($r^2$=0.061, 0.585 and 0.748; Pearson's r=0.779, 0.765 and 0.865 for Groups 1, 2 and 3 respectively). Unlike for eLPI, the correlation between LPI and DCI values was low in Groups 1 and 2 (respective $r^2$=0.201 and 0.038; Pearson's r=0.448 and 0.196), however it was considerably higher in Group 3 ($r^2$=0.519; Pearson's r=0.721). These findings can be interpreted as supportive of the premise that the values of eLPI, like DCI, reflect the total NTBI content in the sample, whereas LPI values might be influenced by variations in serum composition and properties. The latter are related also to two major confounding factors: a. the relative degree of drug compliance which could be as low as 65% in the adult hypertranfused population of patients, which in turn might affect the anti-oxidant capacity of their plasma and b. the mere fact that not all patients complied with the request to refrain from taking the drug in the morning prior to blood testing, as requested.

Example 8

Comparison of LPI Versus eLPI in Chelated Versus Non-Chelated Youngsters

The 3 patient groups are similar in that they are all regularly transfused, mostly thalassemia major patients, but they differ in age and chelation treatment, with the 3-13 year old group being essentially unchelated. Nevertheless, it was of interest to assess the relationship between age and levels of LPI and eLPI. The patients from the 3 centers were analyzed as 3 distinct age categories, 3-13 yrs, 14-28 yrs and 31-61 yrs (this analysis included only those patients in a given center whose ages fitted the assigned age categories). Although the proportion of patients with significant levels of eLPI (≥0.4 µM) was similar in groups 1, 2 and 3 (42, 37 and 38% respectively), the proportion of patients with LPI differed markedly (6, 0 and 19% respectively). The individual values of LPI, eLPI for each patient in the 3 age categories are plotted in FIG. 5. The average LPI and eLPI values of the unchelated 3-13 year olds were 0.0 and 0.4 µM, of the chelated 15-28 year olds were 0.0 and 0.2 µM and of the chelated >30 year olds were 0.2 and 0.4 µM. Thus, the group of unchelated children showed the largest significant mean difference between LPI and eLPI, a rise of 0.4 µ, compared to 0.2 µM in the older, chelated groups. It is hypothesizes that the serum antioxidant activity in unchelated children is sufficiently high to affect detection of LPI, in spite of the presence of NTBI.

Example 9

Optomization of NTA Range in the elPI Assay

Various assays were done in order to determine the optimal NTA level which optimal/maximal NTBI measurement.

Figure 6:
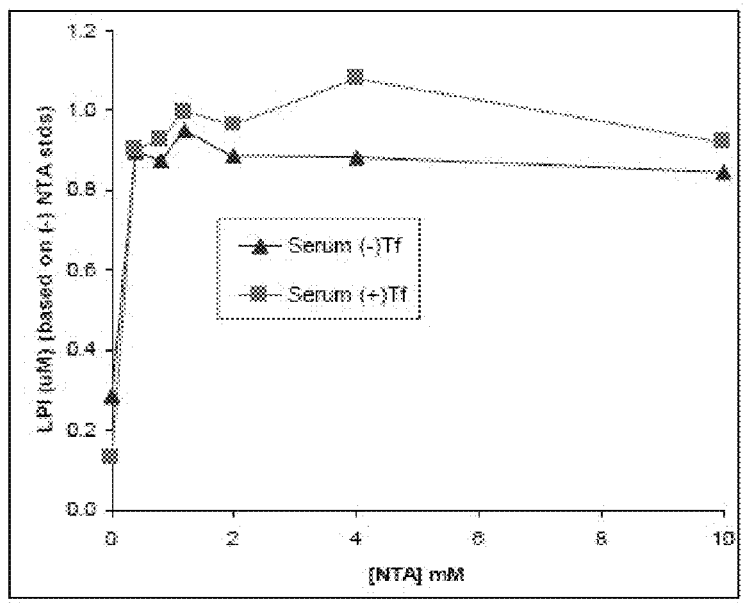
FIG. 6 is a graph showing optimal NTA concentration for measuring eLPI.
Figure 7:
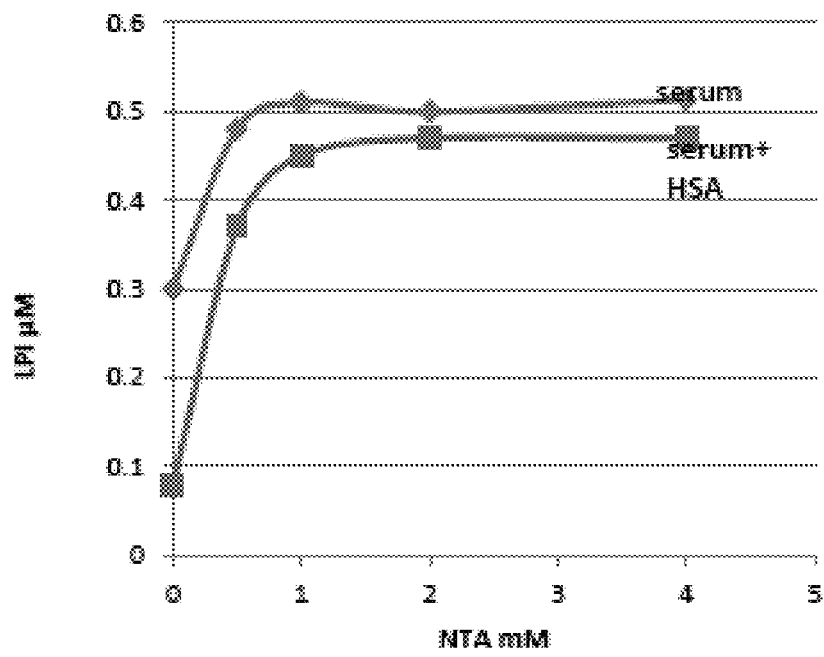
FIG. 7 is a graph showing optimal NTA concentration for measuring eLPI.

Results are shown in FIG. 6. As can be seen NTA levels higher than 0.4 mM allow for optimal/maximal NTBI measurement. At such concentrations the Tf-Fe complex is not disturbed The effect of serum components (which chelate the iron) is overcome by 1 mM NTA as shown in FIG. 7.

Figure 8:
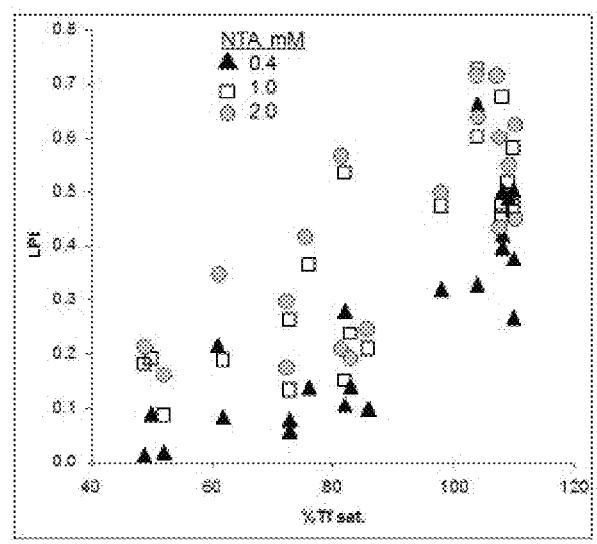
FIG. 8 is a graph showing optimal NTA concentration for measuring eLPI in thelassemic patients sera.

FIG. 8 shows essentially similar results for various concentrations of NTA tested (0.4, 1 and 2 mM) in determining eLPI levels in sera from Thalassaemic patients.

The inhibitory effect of human serum albumin (HSA) on the LPI level can be overcome by higher NTA >1 mM.

In 22 sera from Thalassaemia patients using 1 mM NTA instead of 0.4 mM increased LPI by 0.1±0.1 µM and was essentially the same as to that of 2 mM.

The range of NTA concentrations for attaining optimal LPI was determined 0.4-2 mM.

Discussion

The pathophysiological relevance of NTBI in iron overload conditions is widely accepted because its emergence in plasma denotes an unbalanced state of iron secretion into plasma surpassing the physiological utilization of the metal. The same relevance would apply to plasma Tf-saturation, which at persistently high levels (>70%) is also indicative of iron overload. In addition, NTBI was also hypothesized to be an indicator of impending iron accumulation in extrahepatic (and to some extent also hepatic) tissues. That hypothesis leaned on retrospective clinical observations [30] and on the use of an experimental ex vivo model of iron overloaded cardiomyocytes [31]. In the first, the majority of thalassemia patients with cardiac iron complications (assumed to be associated with cardiac iron accumulation) were found to have high levels of NTBI (detected 48-72 h after withdrawal of treatment) [30], or LPI (detected before daily drug intake) [1,18]. Although the chemical characterization of NTBI is still incomplete, several studies point towards mixed complexes of iron-citrate (free and/or bound to albumin) and iron-albumin as major components [9,10]. The heterogeneous composition of NTBI, which probably varies with the degree and source of iron overload, has hampered the determination of NTBI in the clinical setting, let alone the identification of the iron components relevant to tissue iron overload.

In view of the above, it is not surprising that a gold standard for NTBI determination has not emerged and the values obtained often depend on the assay used [13]. This implies that in practical diagnostic terms using a single NTBI assay method may provide an incomplete picture. Therefore, the objective of this work was to apply two modes of a single method that would simultaneously provide information on at least two major fractions of NTBI—with and without overt redox activity (Table 1). This is accomplished by measuring redox activity of NTBI without and with the iron mobilizing agent NTA, which enables the differentiation between NTBI fractions that are redox-active (termed LPI for overt LPI) and those that are either redox-inactive or whose activity is obscured by various serum components (termed eLPI for total LPI).

NTA is an effective iron-mobilizing agent, as evidenced by its use in several NTBI assay formats [13, 14], where it is required for extracting NTBI in order to render it size-filterable and thereby detectable by various techniques. However, NTA must be used judiciously in order not to mobilize transferrin-bound iron [15], as extraction of even a small fraction (1-5%) of iron from holoTf or from iron-chelates (in chelated patients) can lead to unwarranted overestimation of NTBI [14]. This is particularly the case when traces of chelators might be present in circulation. For this reason the present inventors have restricted the NTA concentration in the eLPI assay to 0.5 mM, even though higher concentrations are tolerated in the assay (FIG. 1 and Breuer et al. data not shown). As shown in FIG. 2, values obtained in the eLPI assay are unaffected by exogenously added holo-transferrrin. In contrast, addition of NTA to the DCI assay, which is based on a fluorescent deferrioxamine derivative, caused extraction of iron from holo-transferrin and its concentration had to be limited to 0.1 mM. Since the addition of 0.1 mM NTA to the DCI assay increased the obtained values by ≤0.1 µM both in model systems (FIG. 2) and in tests with patient sera, NTA-enhanced DCI is not deemed to be more useful than just DCI.

The action of NTA in the eLPI assay may be twofold: mobilization of redox-inactive iron from ligands such as citrate and possibly albumin, and/or enhancement of its redox-activity, as iron-nitriloacetate ligand complexes such as NTA and EDTA are known to undergo reduction-oxidation cycling [24]. The latter effect may explain NTA mediated reversal of LPI inhibition by uric acid.

In vitro measurements of LPI showed that it is highly chelator-accessible (FIG. 3), in agreement with previous studies in patients, where the kinetics of LPI elimination coincided with the kinetics of chelator intake and clearance [1,18,32,33]. These LPI measurements were instrumental in determining chelation regimens that could maintain LPI below a basal level on a diurnal basis and thereby, prevent tissue iron loading [18,32]. This was in line with the implied pathophysiological role of LPI as indicator of impending tissue iron accumulation; because membrane permeant iron is by definition labile (i.e. iron in a given complex is considered chemically labile if it is exchangeable with other metals or between ligands and is redox active).

In contrast to LPI, eLPI was found to be considerably less chelator-sensitive (FIG. 3). The basis for this effect is not clear, as the concentrations of the chelators were in large excess relative to iron and their affinities for iron are many orders of magnitude greater than that of NTA. In general, NTBI assays based on strong chelators and/or mobilizing agents may not be ideally suited for monitoring chelator access to NTBI over the short term (hours to days). This is because in methods like DCI and bleomycin [20], NTBI detection might be biased by the capture of iron from iron-chelates, resulting in overestimation of NTBI. Conversely, mobilizing agents, which solubilize NTBI forms that are not chelator accessible in vivo and may cause ligand exchange and redistribution of NTBI after sample withdrawal, could, in the presence of chelators in the circulation, skew the NTBI values and result in misinterpretation of chelator activity.

Comparison of 3 different thalassemia patient populations revealed that LPI measurements alone do not provide a measurement of the total NTBI content in patient sera. However, when used in conjunction with eLPI, the two parameters provide a picture of the relative contents of redox-active and highly chelator-accessible fraction of NTBI versus the total NTBI. As shown, unchelated children with high serum ferritin values and other indicators of iron overload showed detectable eLPI levels, but almost undetectable LPI levels. The present inventors have attributed this to maintenance of high serum antioxidant activity in this group. In contrast, the values of LPI and eLPI in chelated adults were comparable and generally higher than the younger patients, possibly related to age-dependent decrease in serum antioxidants and higher 1 accumulated body iron burden. This led us to conclude that published values of LPI data in the adult population under active chelation [18,33], can be regarded as representative of total NTBI. However, it cannot excluded that the possibility that the presence of both LPI and eLPI in the well-chelated groups may be indicative of sub-optimal chelation, if patients were non-compliant with drug intake 1-2 days prior to blood testing or vice versa, if they inadvertently took the drug prior to testing.

The present inventors conclude from this study that measurements of the two labile fractions of NTBI (Table 2) have separate and complementary applications. Iron overload levels per se are better represented by the enhanced format eLPI or the equivalent eDCI, with both providing a measure of NTBI. For iron overloaded patients who do not normally undergo chelation therapy, such as in thalassemia intermedia or hereditary hemochromatosis, eLPI or eDCI can provide a sensitive measure of NTBI, irrespective of treatment. However, for monitoring of patients undergoing oral chelation with DFP and DFR, LPI values provide a better indication of extant chelation efficacy than NTBI measurements that depend on strong chelating/extracting probes or mobilizing agents. It is the present view that eLPI, as a reflection of the total NTBI, provides an index of the degree of iron overload of a patient and of the total levels of NTBI, whereas LPI indicates NTBI's potential for incurring direct oxidative damage to tissue and plasma components. Because of the sensitivity of NTBI measurements to chelators, they have the advantage of providing a snapshot of the chelation status of a patient, in contrast to ferritin measurements that can provide long-term information on body iron stores. Chelator sensitivity may also entail a disadvantage of NTBI testing, as it is susceptible to potential errors caused by unreported chelator intake by patients prior to blood testing or vice versa, a poor short term compliance with chelator intake. In conclusion, despite of limitations and/or the caveats inherent in all NTBI assays, it is the present view that LPI is a supplementary indicator of the chelator-accessible iron that can potentially infiltrate cells and/or generate ROS in a patient's plasma, while eLPI (with added NTA) is a more accurate indicator of the total NTBI content. The combined applications of LPI and eLPI in a single assay can provide useful information about the level of iron overload and of the chelator-accessible NTBI for diagnostic and therapeutic purposes.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES other references are cited throughout the document

1. Cabantchik Z I, Breuer W, Zanninelli G, Cianciulli P. LPI-labile plasma iron in iron overload. Best Pract Res Clin Haematol 2005; 18:277-287.
2. Hider R C, Silva A M, Podinovskaia M, Ma Y. Monitoring the efficiency of iron chelation therapy: the potential of nontransferrin-bound iron. Ann NY Acad Sci 2010; 1202: 94-99.
3. Graham G, Bates G W, Rachmilewitz E A, Hershko C. Nonspecific serum iron in thalassemia: quantitation and chemical reactivity. Am J Hematol 1979; 6:207-217.
4. Porter J B. Pathophysiology of transfusional iron overload: contrasting patterns in thalassemia major and sickle cell disease Hemoglobin 2009; 33:S37-S45.
5. Bradley SJ, Gosriwitana I, Srichairatanakool S, et al. Non-transferrin-bound iron induced by myeloablative chemotherapy. Brit J Haematol 1997; 99:337-343.

6. Gosriwatana I, Loreal 0, Lu S, et al. Quantification of non-transferrin-bound iron in the presence of unsaturated transferrin. Anal Biochem 1999; 273:212-20.
7. Le Lan C, Loréal O, Cohen T, et al. Redox active plasma iron in C282Y/C282Y hemochromatosis. Blood 2005; 105:4527-4531.
8. Pootrakul P, Breuer W, Sametband M, et al. Labile plasma iron (LPI) as an indicator of chelatable plasma redox activity in iron overloaded beta-thalassaemia/HbE patients treated with an oral chelator. Blood 2004; 104; 1504-1510.
9. Evans R W, Rafique R, Zarea A, et al. Nature of non-transferrin-bound iron: studies on iron citrate complexes and thalassemic sera. J Biol Inorg Chem 2008; 13:57-74.
10. Silva A M, Hider R C. Influence of non-enzymatic post-translation modifications on the ability of human serum albumin to bind iron Implications for non-transferrin-bound iron speciation. Biochim Biophys Acta 2009; 1794: 1449-1458.
11. Hershko C, Graham G, Bates G W, Rachmilewitz E A. Non-specific serum iron in thalassaemia: an abnormal serum iron fraction of potential toxicity. Brit J Haematol 1978; 40:255-263.
12. Breuer W, Hershko C, Cabantchik Z I. The importance of non-transferrin bound iron in disorders of iron metabolism. Transfus Sci 2000; 23:185-191.
13. Jacobs E M, Hendriks J C, van Tits B L, et al. Results of an international round robin for the quantification of serum non-transferrin-bound iron: Need for defining standardization and a clinically relevant isoform. Anal Biochem 2005; 341:241-250.
14. Singh S, Hider R C, Porter J B. A direct method for quantification of non-transferrin-bound iron. Anal Biochem 1990; 186:320-323.
15. Kolb, A M, Smit N P, Lentz-Ljuboje R, et al. Non-transferrin bound iron measurement is influenced by chelator concentration Anal Biochem 2009; 385:13-19.
16. Breuer W, Cabantchik Z I. A fluorescence-based one-step assay for serum non-transferrin-bound iron. Anal Biochem 2001; 299:194-202.
17. Esposito B P, Breuer W, Sirankapracha P, et al. Labile plasma iron in iron overload: redox activity and susceptibility to chelation. Blood 2003; 102:2670-2677.
18. Zanninelli G, Breuer W, Cabantchik Z I. Daily labile plasma iron as an indicator of chelator activity in Thalassaemia major patients. Brit J Haematol 2009; 147:744-751.
19. Breuer W, Ermers M J, Pootrakul P, et al. Desferrioxamine-chelatable iron a component of serum non-transferrin-bound iron used for assessing chelation therapy. Blood 2001; 97:792-798.
20. Evans P J, Halliwell B. Measurement of iron and copper in biological systems: bleomycin and copper-phenanthroline assays. Meth Enzymol 1994; 233:82-89.
21. Hershko C, Konijn A M, Nick H P, et al. ICL670A: a new synthetic oral chelator: evaluation in hypertransfused rats with selective radioiron probes of hepatocellular and reticuloendothelial iron stores and in iron-loaded rat heart cells in culture. Blood 2001; 97:1115-1122.
22. Link G, Konijn A M, Breuer W, et al. Exploring the "iron shuttle" hypothesis in chelation therapy: effects of combined deferoxamine and deferiprone treatment in hypertransfused rats with labeled iron stores and in iron-loaded rat heart cells in culture. J Lab Clin Med 2001; 138:130-138.
23. Link G, Ponka P, Konijn A M, et al. Effects of combined chelation treatment with pyridoxal isonicotinoyl hydrazone analogs and deferoxamine in hypertransfused rats and in iron-loaded rat heart cells. Blood 2003; 101:4172-4179.
24. Burkitt M J, Gilbert B C. Model studies of the iron-catalysed Haber-Weiss cycle and the ascorbate-driven Fenton reaction. Free Rad Res Com 1990; 10:265-280.
25. Ames B N, Cathcart R, Schwiers E, Hochstein P. Uric acid provides an antioxidant defense in humans against oxidant- and radical-caused aging and cancer: A hypothesis. Proc Natl Acad Sci USA 1981; 78:6858-6862.
26. Roche M, Rondeau P, Singh N R, et al. The antioxidant properties of serum albumin FEBS Lett 2008; 582:1783-1787.
27. Pollack S, Vanderhoff G, Lasky F. Iron removal from transferrin. An experimental study. Biochim Biophys Acta 1977; 497:481-487.
28. Birkett D J, Myers S P, Sudlow G. The fatty acid content and drug binding characteristics of commercial albumin preparations. Clin Chim Acta 1978; 85: 253-258.
29. Evans P, Kayyali R, Hider R C, et al. Mechanisms for the shuttling of plasma non-transferrin-bound iron (NTBI) onto deferoxamine by deferiprone. Transl Res 2010; 156: 55-67.
30. Piga A, Longo F, Duca L, et al. High nontransferrin bound iron levels and heart disease in thalassemia major. Am J Hematol 2009; 84:29-33.
31. Glickstein H, Ben-El R, Link G, et al. Action of chelators in iron-loaded cardiac cells: Accessibility to intracellular labile iron and functional consequences. Blood 2006; 108: 3195-3203.
32. Daar S, Pathare A, Nick H, et al. Reduction in labile plasma iron during treatment with deferasirox a once-daily oral iron chelator in heavily iron-overloaded patients with beta-thalassaemia. Eur J Haematol 2009; 82:454-457.
33. Greenberg P L, Koller Calif., Cabantchik Z I, et al. Prospective Assessment of Effects on Iron Overload Parameters of Deferasirox Therapy in Patients with Myelodysplastic Syndromes. Leuk Res 2010; 34:1560-5.

What is claimed is:

1. A method of quantifying a ligand-bound fraction of redox-active non-transferrin bound iron (NTBI) in a biological fluid, the method comprising:
    (a) quantifying enhanced labile plasma iron (eLPI) in a first sample of the biological fluid, wherein said eLPI consists of both ligand-bound and non-ligand-bound redox-active NTBI iron, comprising:
        (i) contacting a sample of the biological fluid with a reducing agent to obtain redox-active iron;
        (ii) contacting said sample of the biological fluid with a nitrilotriacetate (NTA) at a concentration of 0.4-2 mM to mobilize ligand-bound redox-active non-transferrin bound iron in said sample;
        (iii) contacting said sample of the biological fluid of step (a)(ii) with an indicator including an iron binding moiety and fluorophore; and
        (iv) detecting and quantifying a fluorescent signal of said fluorophore thereby quantifying the eLPI in the biological sample,
    (b) quantifying the labile plasma iron (LPI) in a second sample of the biological fluid, wherein said LPI consists of non-ligand bound redox-active non-transferrin bound iron NTBI, comprising:
        (i) contacting said second sample of the biological fluid with a reducing agent to obtain redox active iron;
        (ii) contacting said second sample of the biological fluid of step (b)(i) with an indicator including an iron binding moiety and fluorophore; and
        (iii) detecting and quantifying a fluorescent signal of said fluorophore thereby quantifying the LPI in the biological sample, and (c) subtracting the LPI from eLPI, thereby quantifying the ligand-bound fraction of redox-active non-transferrin bound iron (NTBI) in the biological fluid.

2. A method of treating a subject having a disorder associated with abnormal levels of free iron in a biological fluid, the method comprising:
(i) quantifying the ligand-bound fraction of redox-active non-transferrin bound iron (NTBI) in a biological fluid of the subject according to the method of claim 1; and
(ii) treating the subject with a chelation therapy.

3. The method of claim 2, wherein (i) is effected prior to (ii).

4. The method of claim 2, wherein (i) is effected following (ii).

5. The method of claim 2, wherein (i) is effected prior to (ii) and following (ii).

6. The method of claim 1, wherein said concentration of said NTA is 0.5-1 mM.

7. The method of claim 1, wherein said iron binding moiety comprises an iron binding protein selected from the group consisting of, lactoferrin, transferrin, ferritin, Ferric uptake repressor (FUR) protein, calcineurin, acid phosphatase and ferredoxin.

8. The method of claim 1, wherein said iron binding moiety comprises an iron chelator selected from the group consisting of desferrioxamine, Deferasirox, FBS0701, phenanthroline, ethylene diamine tetra-acetic acid (EDTA), diethylene triamine-pentaacetic acid (DTPA) and N,N'-bis[2-hydroxybenzoyl]ethylene diamine-N,N'-diacetic acid (HBED).

9. The method of claim 1, wherein said indicator comprises a chimeric protein.

10. The method of claim 1, wherein said biological fluid is a serum or a plasma.

11. The method of claim 1, wherein said biological fluid is selected from the group consisting of as blood, serum, plasma, lymph, bile fluid, urine, saliva, sputum, synovial fluid, semen, tears, cerebrospinal fluid, bronchioalveolar large fluid, ascites fluid and pus.

12. The method of claim 1, wherein said biological fluid is of a subject having thalassemia.

13. The method of claim 1, wherein said biological fluid is of a subject having a medical condition selected from the group consisting of hemolytic diseases hemoglobinopathies, thalassemia, thalassemia major, anemia, sickle cell anemia, aplastic anemia, megaloblastic anemia, myelodysplasia, diseases which require repeated transfusions, diseases which require dialysis, hereditary hemachromatosis, cancer, heart diseases, Megaloblastic Dysplasia Syndrome (MDS), iron poisoning and rheumatoid arthritis and diabetes.

14. The method of claim 1, wherein said signal generating moiety comprises a fluorophore selected from the group consisting of Fluorescein, Rhodamine, nitrobenzfurazan, fluorogenic β-galactosidase, a green fluorescent protein and coumarin.

15. The method of claim 1, further comprising contacting said sample with an apo-transferrin binding metal other than iron prior to step (a)(ii).

16. The method of claim 15, wherein said apo-transferrin binding metal other than iron is cobalt or gallium.

17. The method of claim 1, wherein said reducing agent is selected from the group consisting of ascorbic acid, dithionite, dithiothreitol or mercaptoacetic acid.

18. The method of claim 1, wherein said indicator is attached to a microparticle.

19. The method of claim 18, wherein said detecting is effected by FACS.

20. The method of claim 1, wherein said detecting is effected by a fluorescence plate reader.

21. The method of claim 1, wherein said biological fluid is of a subject has not been exposed to chelation treatment.

22. The method of claim 1, wherein said biological fluid is of a subject exposed to chelation treatment not more than 24 hours prior to quantifying.

23. A method of determining a presence, absence or risk of a disorder associated with abnormal levels of free iron in a biological fluid of a subject, the method comprising:
(a) determining the ligand-bound fraction of redox-active non-transferrin bound iron (NTBI) in the biological fluid of the subject according to claim 1; and
(b) determining in the subject based on said levels a presence, absence or risk of the disorder associated with abnormal free iron levels.

24. A method of determining subject's compliance to chelation therapy, the method comprising:
(a) retrieving a biological fluid of a subject in need thereof 2-24 hours following alleged administration of the chelation therapy; and
(b) quantifying the ligand-bound of redox-active non-transferrin bound iron (NTBI) in said biological fluid of said subject according to claim 1, wherein an increase the ligand bound fraction of redox-active non-transferrin bound iron (NTBI) is indicative of subject's compliance.

25. A method of determining efficacy of treatment of a disorder associated with abnormal levels of free iron in a biological fluid, the method comprising:
(a) treating a subject in need thereof using a medicament for the disorder associated with abnormal free iron levels; and
(b) determining the ligand-bound fraction of redox-active non-transferrin bound iron (NTBI) in a biological fluid or cells of said subject according to claim 1, wherein a change in said fraction following said treating is indicative of treatment efficacy.

26. The method of claim 25, wherein said medicament comprises iron chelation therapy, and whereas a reduction in said fraction following said therapy is indicative of efficacious treatment.

27. The method of claim 2, wherein said disorder associated with abnormal levels of free iron is selected from the group consisting of hemolytic diseases hemoglobinopathies, thalassemia, thalassemia major, anemia, sickle cell anemia, aplastic anemia, megaloblastic anemia, myelodysplasia, diseases which require repeated transfusions, diseases which require dialysis, hereditary hemachromatosis, cancer, heart diseases, Megaloblastic Dysplasia Syndrome (MDS), iron poisoning, end stage kidney disease, cancer, transplantation-associated anemia, rheumatoid arthritis and diabetes.

28. The method of claim 1, wherein step (a)(ii) is effected prior to (a)(i).

* * * * *